United States Patent
Miller et al.

(10) Patent No.: US 10,441,434 B2
(45) Date of Patent: Oct. 15, 2019

(54) METHODS, DEVICES AND SYSTEMS FOR COMPUTER-ASSISTED ROBOTIC SURGERY

(71) Applicants: Denise A. Miller, Fremont, CA (US);
Rose A. Cipriano, Fremont, CA (US);
Lu Li, Fremont, CA (US)

(72) Inventors: Denise A. Miller, Fremont, CA (US);
Rose A. Cipriano, Fremont, CA (US);
Lu Li, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 0 days.

(21) Appl. No.: 14/417,446

(22) PCT Filed: Mar. 13, 2014

(86) PCT No.: PCT/US2014/025458
§ 371 (c)(1),
(2) Date: Jan. 26, 2015

(87) PCT Pub. No.: WO2014/159924
PCT Pub. Date: Oct. 2, 2014

(65) Prior Publication Data
US 2016/0038243 A1 Feb. 11, 2016

Related U.S. Application Data

(60) Provisional application No. 61/780,878, filed on Mar. 13, 2013.

(51) Int. Cl.
*A61B 34/10* (2016.01)
*A61B 34/00* (2016.01)
(Continued)

(52) U.S. Cl.
CPC ............ *A61F 2/4603* (2013.01); *A61B 17/17* (2013.01); *A61B 34/10* (2016.02);
(Continued)

(58) Field of Classification Search
CPC ...................................................... A61B 34/10
See application file for complete search history.

(56) References Cited

U.S. PATENT DOCUMENTS 5,086,401 A * 2/1992 Glassman ................. A61F 2/46
606/53
5,824,085 A 10/1998 Sahay et al.
(Continued)

OTHER PUBLICATIONS

Kazanzides, Peter, Mittelstadt, Brent D., Musits, Bela L., Bargar, William L., Zuhars, Joel F., Williamson, Bill, Cain, Phillip W. and Carbone, Emily J., "An Integrated System for Cementless Hip Replacement"; Robotics and medical imaging technology enhance precision surgery; IEEE Engineering in Medicine and Biology; May/Jun. 1995; pp. 307-313, © 1995.
(Continued)

*Primary Examiner* — Jacqueline Woznicki
(74) *Attorney, Agent, or Firm* — Avery N. Goldstein; Blue Filament Law PLLC

(57) ABSTRACT

Methods, devices and systems for the planning and execution of computer-assisted robotic surgery are provided. The methods include methods to collect information about bones and prostheses, use the information to create virtual models and simulations, optionally receive input based on user discretion in generating the cut file, and to generate instruction for the execution of cut paths during the surgery. The system and devices include computers and peripherals and set-ups to link the components together into functional systems.

7 Claims, 7 Drawing Sheets

(51) Int. Cl.
*A61F 2/30* (2006.01)
*A61F 2/46* (2006.01)
*A61B 17/17* (2006.01)
*A61B 17/15* (2006.01)

(52) U.S. Cl.
CPC .......... *A61F 2/30942* (2013.01); *A61B 17/15* (2013.01); *A61B 34/00* (2016.02); *A61B 2034/101* (2016.02); *A61B 2034/102* (2016.02); *A61B 2034/104* (2016.02); *A61B 2034/105* (2016.02); *A61B 2034/107* (2016.02); *A61B 2034/108* (2016.02)

(56) References Cited

U.S. PATENT DOCUMENTS

| | | | | |
|---|---|---|---|---|
| 6,301,495 | B1 * | 10/2001 | Gueziec | A61B 6/00 600/407 |
| 2003/0176860 | A1 * | 9/2003 | Shimura | A61B 34/10 606/53 |
| 2004/0102866 | A1 * | 5/2004 | Harris | G06T 17/00 700/117 |
| 2007/0219561 | A1 | 9/2007 | Lavallee et al. | |
| 2008/0009697 | A1 * | 1/2008 | Haider | A61B 17/14 600/407 |
| 2009/0306676 | A1 | 12/2009 | Lang et al. | |
| 2010/0063496 | A1 * | 3/2010 | Trovato | G06T 7/0012 606/34 |
| 2012/0323244 | A1 | 12/2012 | Cheal et al. | |
| 2013/0035690 | A1 | 2/2013 | Mittelstadt et al. | |
| 2013/0035696 | A1 * | 2/2013 | Qutub | A61B 17/16 606/130 |
| 2013/0245801 | A1 * | 9/2013 | Schroeder | A61F 2/30 700/98 |
| 2013/0289570 | A1 * | 10/2013 | Chao | A61B 17/1764 606/88 |
| 2014/0244220 | A1 | 8/2014 | McKinnon et al. | |

OTHER PUBLICATIONS

Extended European Search Report dated Mar. 13, 2017 for European Application No. 14775267 filed Mar. 13, 2014.
Cited U.S. 2014/0244220 A1 as U.S. equivalent to WO2013/013170 A1.

* cited by examiner

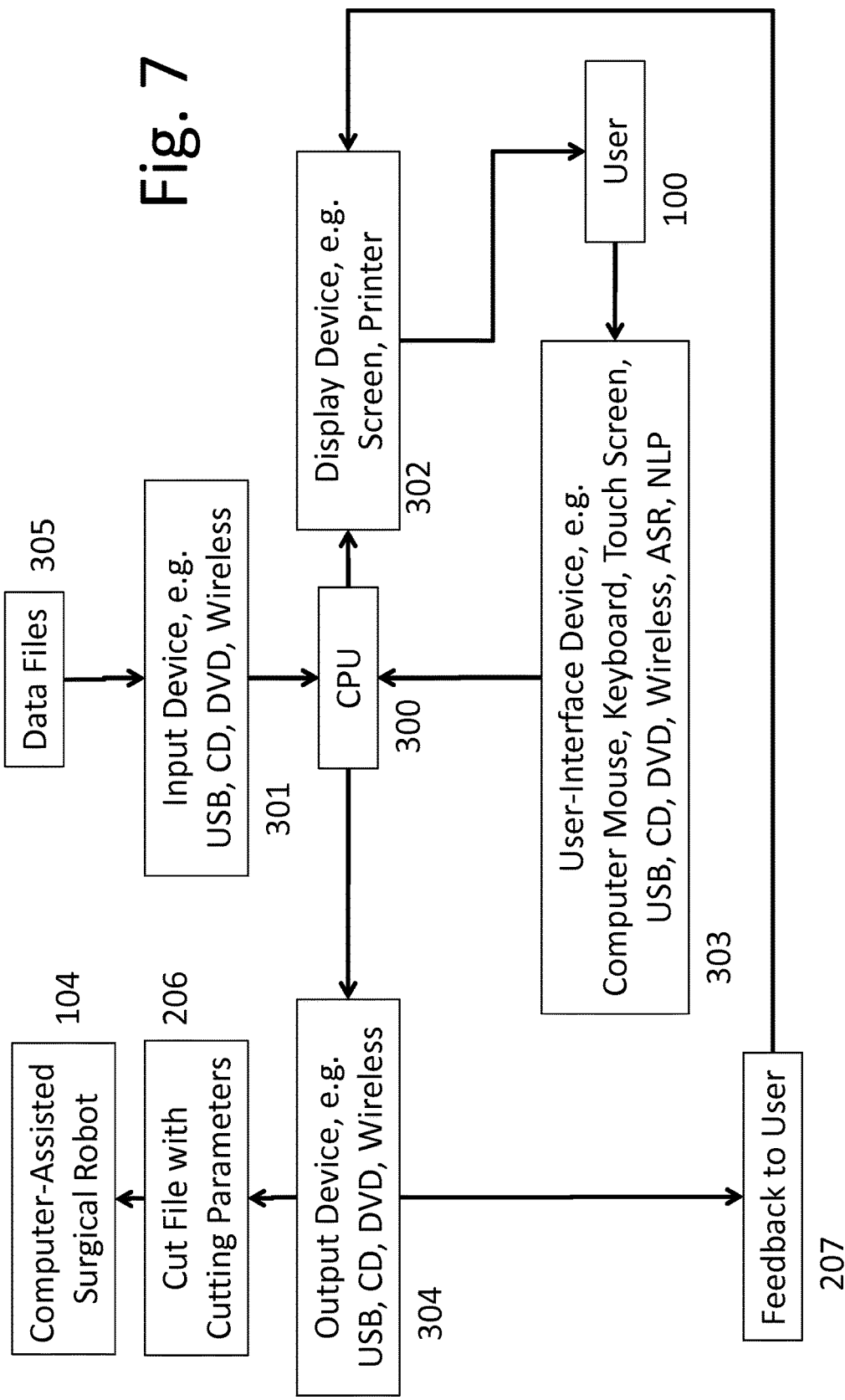

METHODS, DEVICES AND SYSTEMS FOR COMPUTER-ASSISTED ROBOTIC SURGERY

CROSS-REFERENCE TO RELATED APPLICATION

This application claims priority of U.S. Provisional Patent Application Ser. No. 61/780,878 filed Mar. 13, 2013, which is incorporated herein by reference.

FIELD OF THE INVENTION

This invention generally relates to the orthopedic prosthesis implantation surgery, and more specifically to a new and useful method and system for planning and executing the implantation surgery of an orthopedic prosthesis in bone.

BACKGROUND OF THE INVENTION

Throughout a lifetime, bones and joints become damaged and worn through normal use and traumatic events. This degradation of the joints involving the articular cartilage and subchondral bone is known as arthritis and results in symptoms including joint pain, tenderness, stiffness, and potentially locking.

Joint replacement arthroplasty is an orthopedic procedure in which the arthritic surface of the joint is replaced with a prosthetic component. It is considered the primary form of treatment to relieve joint pain or dysfunction that may limit mobility. During an arthroplasty procedure, the ends of the bone and articular cartilage may be resurfaced or replaced.

The accurate placement and alignment of a prosthesis is a large factor in determining the success of a joint arthroplasty procedure. A slight misalignment may result in poor wear characteristics, reduced functionality, and a decreased longevity. To obtain accurate and durable implantation, one must not only achieve correct alignment of the prosthesis with the bone, but also correct positioning of the prosthesis within the bone to achieve reliable and durable anchoring.

In order to achieve these objectives, computer-assisted methods and systems have been developed that can provide three-dimensional models of the bone, models of the prosthesis, and model-in-model simulations. Based on these models and simulations, the methods and systems can generate three-dimensional models of a volume of bone to be removed in a computer-assisted surgical procedure, and guide the optimal positioning of these removed volumes within the bone. A cut-file with cutting parameters specifying a cut path to remove the volume of bone can then be generated, and can be used in computer-assisted surgery.

FIG. 1 illustrates a pathway according to commonly owned prior art technology (U.S. Pat. No. 5,824,085 to Sahay, A. et al.). There is a linear flow of steps, starting with the generation 001 of a bone model from a scanned image of a bone, the selection 002 of a prosthesis model from a library of prosthesis models, the generation 003 of a cavity model based on the prosthesis model, and the positioning 004 of the cavity model within the bone model.

Before the introduction of robot-assisted orthopedic surgery, the entire procedure, from planning to preparation to execution, was performed by the physician and their staff. The strength of this approach was an optimal use of the physician's personal skill and experience. However, the level of mechanical control was determined by the limitations of human skill and dexterity.

With the introduction of computer-assisted robotic surgery in the 1990s, the levels of mechanical control have greatly improved. Unfortunately, in part due to the boundaries of computer technology at the time, the scope of assistance that can be provided by the computer may be restricted to the execution of a cut file with cut parameters that are based on limited input, for instance input that is limited to the dimensions of a cutting cavity correlating to a particular prosthesis, and its position in a bone model. The use of one of the strengths of the pre-computer era, the physician's skill and experience, is reduced in favor of the mechanical control.

Examples of the consequences thereof are the fact that in the currently available technology a pre-existing set of cut files, based on the design of the prosthesis, may actually cause cutting interference with soft tissue, or may require cutting unnecessary areas using robotic assistance when the physician may prefer to cut certain regions without assistance.

Another example is the inability for the physicians to enter preferences based on personal experience, or based on patient-specific factors like age, life expectancy, body weight and expected physical activity.

Therefore, there is a need to improve patient outcomes by enabling more physician-specified input to be incorporated in the planning and execution of computer-assisted robotic surgery.

SUMMARY OF THE INVENTION

Methods, devices and systems for the planning and execution of computer-assisted robotic surgery are provided. The methods include methods to collect information about bones and prostheses, use the information to create virtual models and simulations, optionally receive input based on user discretion in generating the cut file, and to generate instruction for the execution of cut paths during the surgery. The system and devices include computers and peripherals and set-ups to link the components together into functional systems.

BRIEF DESCRIPTION OF THE DRAWINGS

FIG. 7 illustrates an embodiment of a computer system according to the present invention.

DESCRIPTION OF THE INVENTION

The present invention has utility in improving patient outcomes by combining customized physician input with computer-assisted control of robotic orthopedic surgery. Embodiments of the invention provide systems and methods for planning and executing a surgical procedure, such as the incorporation of a prosthesis within a bone. The invention is particularly useful in planning a coupling of a prosthesis to a long bone, such as the femur, tibia, humerus, ulna, and radius. Planning the position of a prosthesis in such long bones will be particularly useful in conjunction with robotic surgical procedures, such as joint replacement, with specific procedures including total hip joint replacement, knee joint replacement, long bone osteotomy, and the like. The present invention, however, is not limited to such robotic procedures and will be equally useful in manual surgical, diagnostic, and other medical procedures where it is necessary to align a pre-obtained image of a long bone within an actual coordinate space, such as an operative space. Such manual systems and procedures include computer-assisted surgical procedures that employ optical surgical measurement tools, passive electromechanical devices, and the like.

The methods of inventive disclosed technology generally include the steps of generating a bone model from a scanned image of a bone, creating a prosthesis model, generating a model of a cavity in the bone to accommodate the prosthesis based on the prosthesis model and/or the bone model, and positioning the cavity model within the bone model.

With the development of increased computing speed and interface versatility, it is now technically feasible to greatly increase the number of planning input parameters provided to a Central Processing Unit (CPU) of a computer to generate optimized surgical output parameters. This has opened up the possibility of introducing a significantly improved treatment paradigm, which is a hybrid of the flexibility of patient- and physician-centered planning with the accuracy and precision of computer-assisted planning and execution. Combining optimal individualized planning with computer-assisted control during the surgical procedure may significantly enhance patient outcomes.

The present invention discloses methods, devices and systems that allow for additional, individual customization by a physician based on a multitude of considerations, including but not limited to:

Prosthesis: Design and dimensions
Bone: Anatomy, physiology, pathology, medical history
Patient: Age/life expectancy, weight, lifestyle/physical activity
Physician: Experience, specific skill sets, personal preference The following description of inventive embodiments is not intended to limit the invention to these specific embodiments, but rather to enable any person skilled in the art to make and use this invention.

Methods

Figure 1:
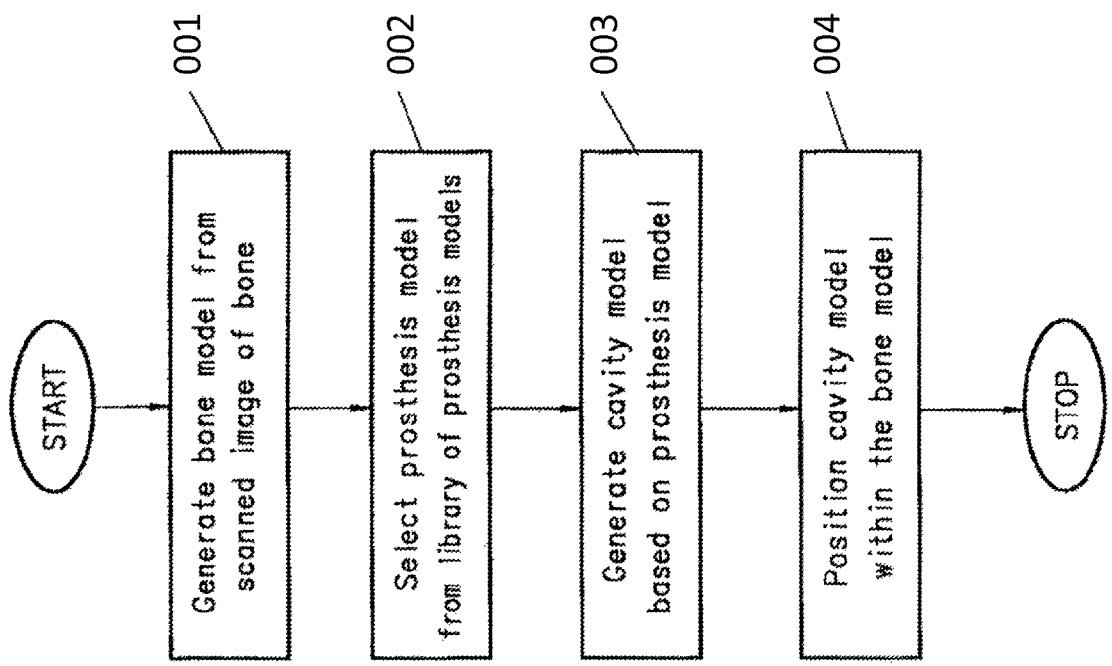
FIG. 1 illustrates a prior art workflow according to previously disclosed technology.
Figure 2:
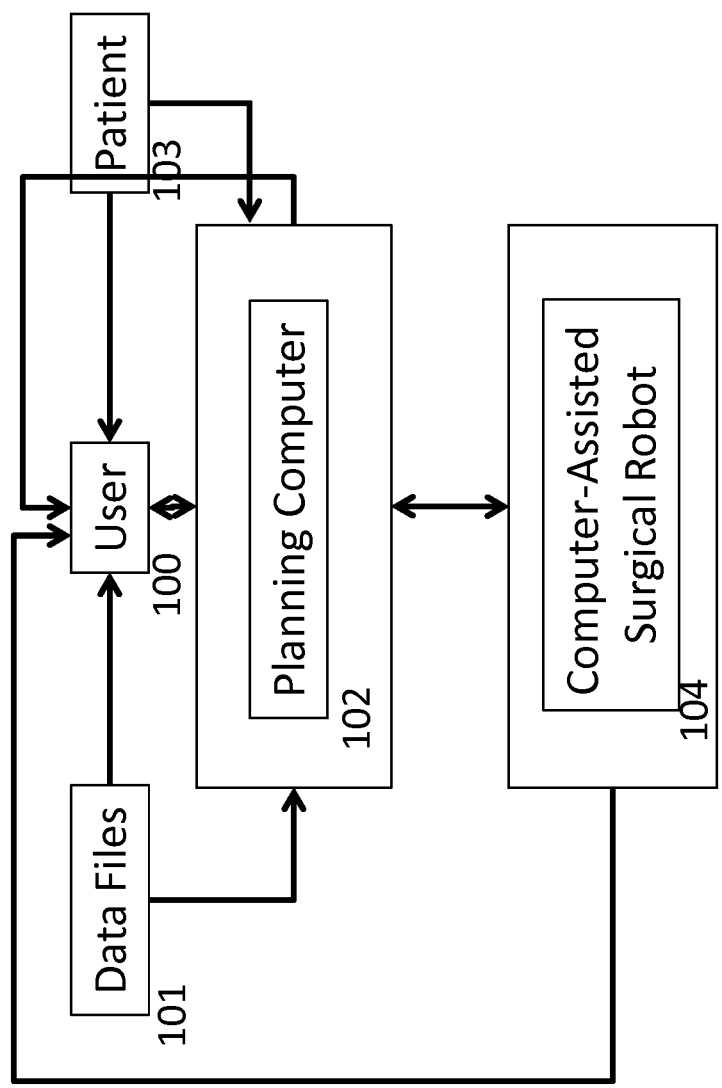
FIG. 2 illustrates a high level workflow according to the present invention.

An example of a high level workflow falling under the scope of the present invention is shown in FIG. 2. A user 100 may have a central function, in which information can be received from a data file 101, a patient 103, a planning computer 102, and a computer-assisted surgical robot 104. The user 100 may also issue commands to the planning computer 102 and the computer-assisted surgical robot 104. The planning computer 102 and the computer-assisted surgical robot 104 may be in direct communication with each other.

The scope of the present invention does not require all components shown in FIG. 2 to be present or used when present, nor is the scope limited to these components. For instance, a user may use a planning computer, but perform the surgery manually without a computer-assisted robot. Likewise, one or more users 100 may be present. For instance, the planning computer 102 may be operated by a different user than the computer-assisted surgical robot 104. Additionally, the various operations do not have to be conducted simultaneously, or even in conjunction with each other. For instance, the planning may be performed at a different medical facility than the surgery, and the invention does not limit in any way the period of time between the planning and the surgery.

Figure 3:
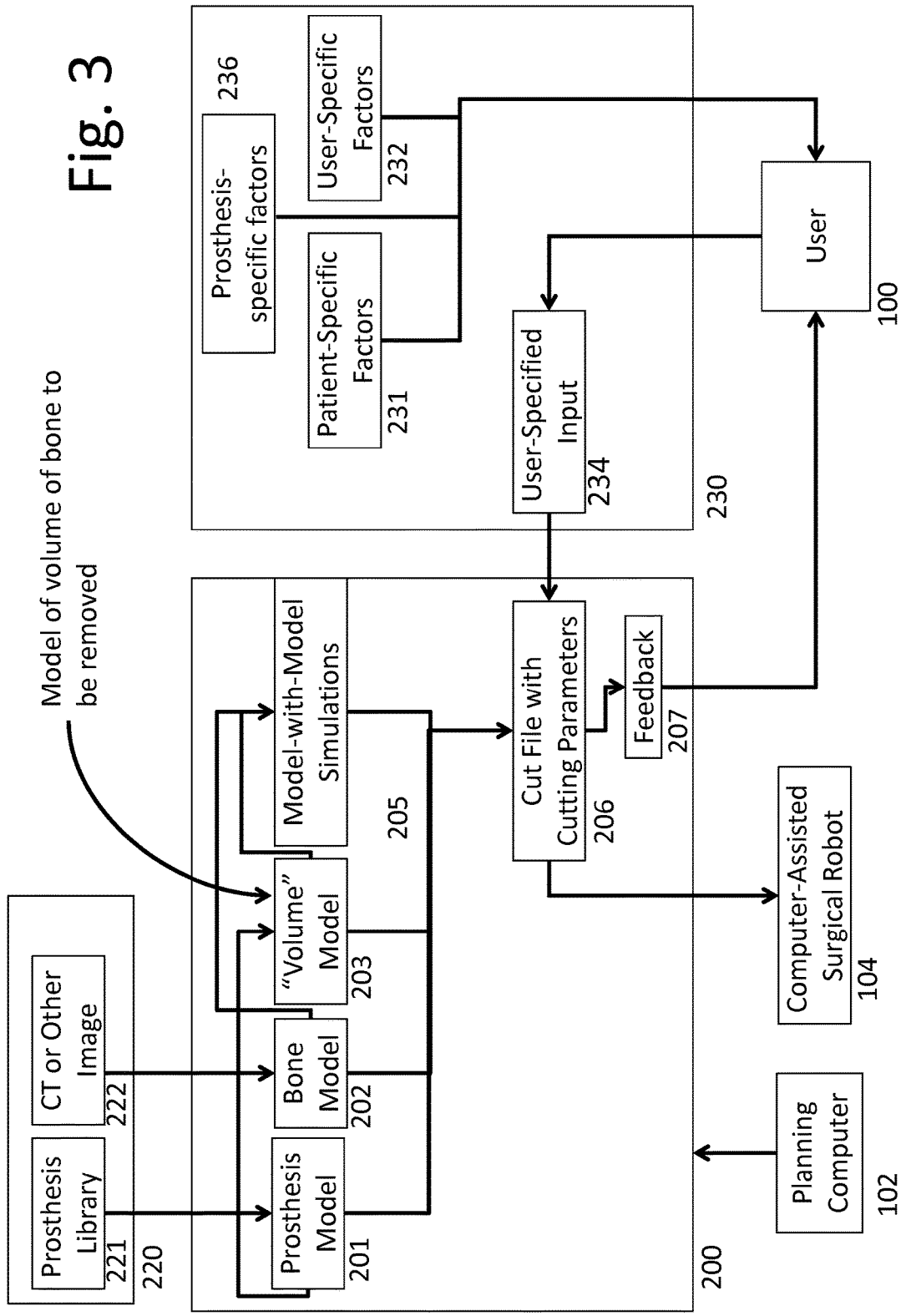
FIG. 3 illustrates a detailed workflow according to the present invention.

FIG. 3 illustrates a schematic representation of a preferred embodiment of a method for planning a coupling of a prosthesis to a bone. The method may include the steps of providing one or more of a model of the prosthesis 201, a model of the bone 202, and a model of a volume of bone to be removed, referred to as the "volume model", 203 to accommodate the coupling of the prosthesis to the bone, of generating a cut file 206 with cutting parameters to specify at least one cut path configured to create the volume of bone to be removed 203. In specific inventive embodiments, one is receiving input 234 based on user discretion in generating the cut file 206.

In the present disclosure, the term "model of the volume of bone to be removed" refers not only to a quantitative measure of the volume of bone to be removed, but also to the three-dimensional geometric shape of that volume.

This exemplary embodiment is one of many options that fall under the scope of the present invention and that will be apparent without undue experimentation to those with ordinary skills in the art.

In the representation of FIG. 3 block 220 contains machine-readable information from a prosthesis library 221 and from computerized tomography (CT), radiography (digitized X-ray images), magnetic resonance imaging (MRI), or other medical image file 222 of a bone intended to receive the prosthesis. The prosthesis model 201 may be generated, or selected from a library or database of implant designs of different prostheses 221, which may be stored using a suitable medium, either in tangible form like a CD or hard-drive, or in a cloud-based service. The implant designs may be in the form of computer aided design (CAD) models which may be available from the manufacturers.

The model of a bone 202 may be obtained or generated using a conventional medical imaging technique, such as computerized tomography (CT), radiography (digitized X-ray images), magnetic resonance imaging (MRI), and the like. The image 222 may be obtained in or converted to a digital form to produce an image data set which is suitable for digital manipulation using conventional computerized image processing equipment and software.

Block 200 illustrates the workflow within the planning computer 102.

The method may generate a model of the volume of bone to be removed 203 from the model of the prosthesis 201.

The method may also generate the model of the volume of bone to be removed 203 from the model of the bone 202.

The method may generate a simulation 205 of the model of the bone 202 with the model of the volume of bone to be removed 203, The method may also generate a simulation 205 of the model of the volume of bone to be removed 203 with the model of the prosthesis 201, and specifically a simulation wherein the model of the prosthesis 201 is positioned at least partially within the model of the volume of bone to be removed 203.

The method may also generate a simulation of the model of the bone 202 with the model of the prosthesis 201, and specifically a simulation wherein the model of the prosthesis 201 is positioned at least partially within the model of bone 202.

The information generated in workflow 200 allows the user 100 to optimize the planned position of the prosthesis in the bone. The information may be used to generate a cut file 206 with cutting parameters specifying a cut path designed to remove the section of bone corresponding to the planned position of the prosthesis in the bone.

In this exemplary embodiment such a cut file 206 may contain instructions for one or more of precut, depth of cut, length of cut, diameter of cut path, regions to be cut, number of cut paths, dimensions of planes, shapes of cut paths, and types and sizes of cutters to be used.

The present invention allows for use of input based on user discretion in generating the cut file. This is illustrated in box 230.

In box 230 the user 100, typically a physician has the option to augment the planning procedure with user-specified input 234 generated at their discretion.

Figure 4:
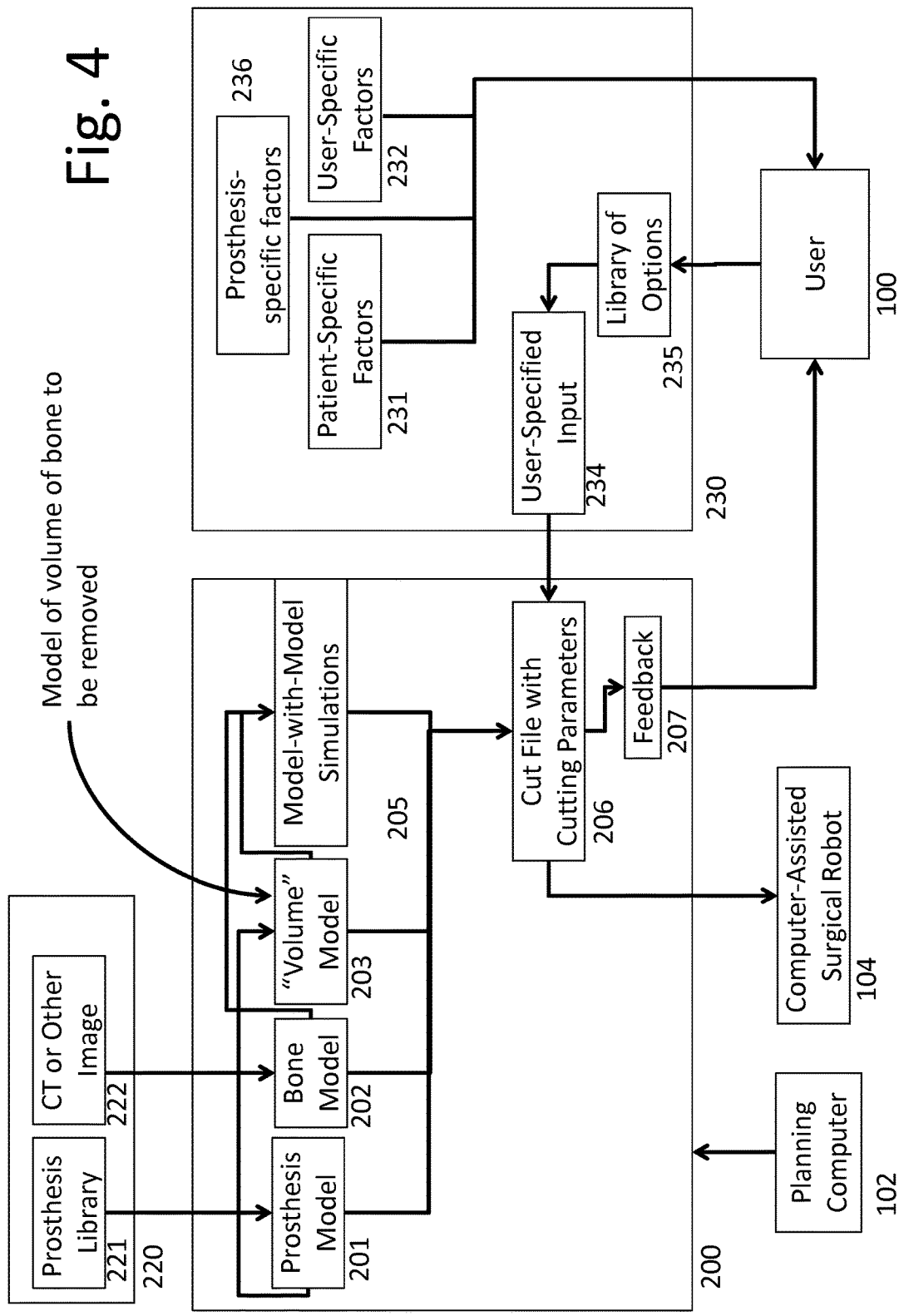
FIG. 4 illustrates the inclusion of a library of options in a workflow according to the present invention.

As illustrated in FIG. 4, the input based on user discretion 234 in generating the cut file 206 may be selected from a pre-populated library of options 235. Limiting the user-specified input 234 to items from a pre-populated library 235 may have advantages in terms of requiring less computing power, reducing cost, improving response times, facilitating operational system validation, and preserving patient safety. For instance, this may be achieved through the use of drop-down menus.

Figure 5:
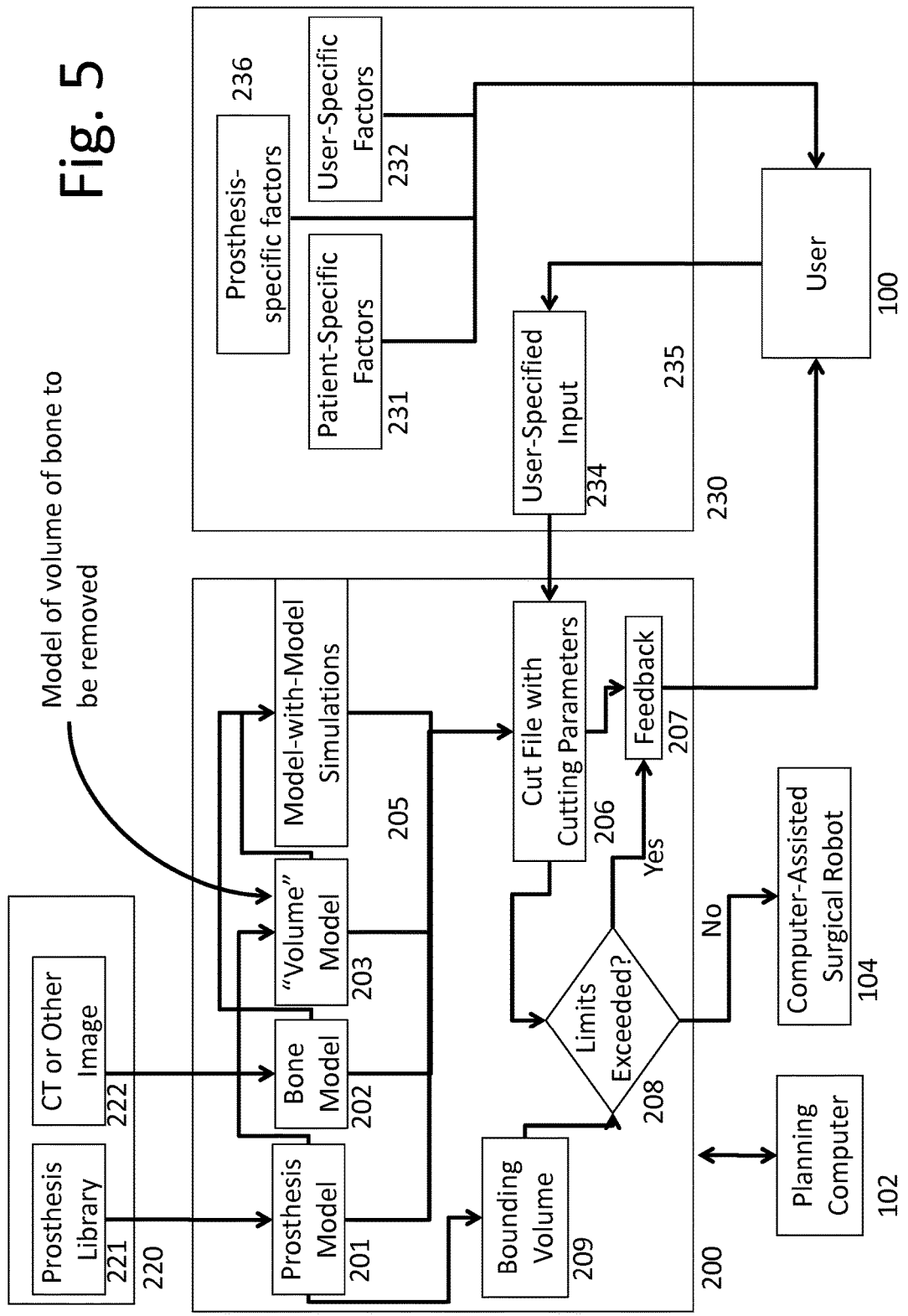
FIG. 5 illustrates the inclusion of a safety check box in a workflow according to the present invention.

As illustrated in FIG. 5, the method may generate a bounding volume 209, wherein the bounding volume 209 can be used to control the volume of the bone to be removed 203. This may be performed as part of a safety procedure.

Safety considerations are often a major factor in the design of medical methods and systems. Safety controls can be incorporated in multiple ways into the methods of this invention. For instance, in certain embodiments pre-determined limits can be set on the input from the workflow in box 220 to the cut file 206, and the user specified input 234 can be limited to pre-determined limits as described in FIG. 4 where the user input 234 is limited to choices selected from a drop-down menu. In such embodiments the safety of the procedure can be assured through validation of controls to the input to the cut file.

Another method of incorporating safety controls is by means of controlling the output from the cut file. This approach is illustrated in the exemplary embodiment in FIG. 5. In this example, a bounding volume 209 for the volume of bone to be removed is generated from the prosthesis model 201. A check-box 208 is incorporated downstream of the cut file 206, and the information from the bounding volume 209 is fed into the check-box 208.

If the volume of bone to be removed, specified by the cut file 206 exceeds the bounding volume 209 derived from the prosthesis model 201, a warning is sent to the feedback 207 to the user who can adjust the user-specified input 234.

Those with ordinary skills in the art will easily be able to design other safety features, for instance features based on critical two-dimensional planes or on linear dimensions, rather than on volumes, and features that are based on other inputs, like the model of the bone or a simulation of the model of the volume of bone to be removed in the model of the bone itself.

More than one safety feature may be included, and more than one source for deriving the safety feature may be used.

The method may allow for the input based on user discretion 234 (FIGS. 3-6) to be based on patient-specific factors 231, user-specific factors 232, and/or prosthesis-specific factors 236. For instance, the user 100 may want to take into account a personal judgment, based on patient-specific factors 231, like patient age, weight, life expectancy, physical activity, kinematic joint alignment, and the like. Also, a physician may have personal preferences, based on skills or experience level, which can be introduced as user-specific factors 232. It should be understood that, since this input is generated at the discretion of the user 100, there may not be a pre-set limit to the type of factors the user 100 wants to take into account. Cost, duration of procedure, capabilities of the surgical robot to be used, availability of revalidation programs etc. are just a few examples of other factors a user 100 may choose to consider.

The method also may allow the input based on user discretion 234 to make modifications to one or more of precut, depth of cut, length of cut, diameter of cut path, regions to be cut, number of cut paths, dimensions of planes, shapes of cuts, and types and sizes of cutters.

Then method may also provide a feedback loop 207 to a user 100 from one or more of the prosthesis model 201, the bone model 202, the model of the volume of bone to be cut 203, the model-with-model simulations 205, and the cut file 206. A user 100 may use this feedback 207 to improve the user-specified input 234 in an iterative process of cut file 206 optimization.

In the examples illustrated so far, the method may be employed pre-operatively.

Figure 6:
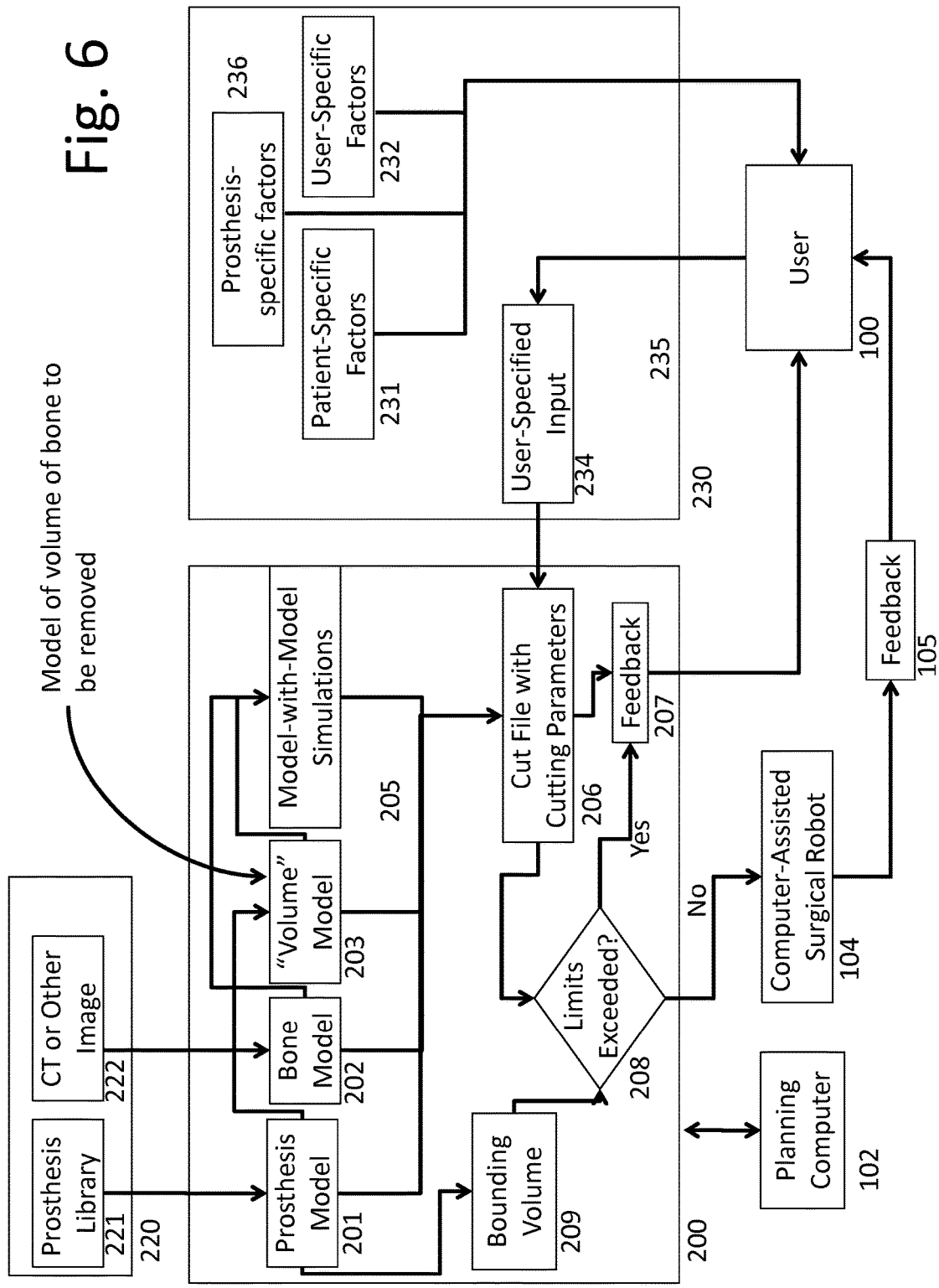
FIG. 6 illustrates the inclusion of feedback from a computer-assisted surgical robot in a workflow according to the present invention.

The method may also be used intra-operatively, as is illustrated in FIG. 6.

FIG. 6 illustrates an exemplary embodiment with an option of performing intra-operative planning, allowing a user 100 to make adjustments to the input 234 for the cut file 206 while the procedure is being carried out.

In this embodiment, instructions from the cut file 206 may be sent to a computer-assisted surgical robot 104 for execution. The robot may be equipped with measurement capabilities, like sensor- or image based technologies. Data about progress from the surgery may be collected real-time, and information sent back as feedback 105 to the user 100. Additionally, the user 100 may see something during cutting that they may want to change. The user 100 will have the option to pause or stop the robotic surgery, and the user 100 can modify the input 234 to the cut file 206 and adjust the cutting parameters specifying the cut path in real time or with minimal delay.

The options for this feedback loop are not limited to feedback 105 directly to the user 100. Those with ordinary skills in the art will easily be able to configure the method to be capable of providing the feedback 105 to other parts of the method, for instance to the model-in-model simulations 205. In this case, a simulation can be generated showing the partially completed the volume of the bone to be removed 203, as it is positioned in the bone model 202, for instance to allow display of the progress of the procedure real-time. Other feedback options include warning signs to check box 208 that the procedure is approaching the bounding volume specified for the prosthesis. Multiple warning- and feedback pathways can be incorporated simultaneously.

The invention also provides a method for generating a cut file 206 with cut parameters specifying at least one cut path for creating a volume of bone to be removed for coupling a prosthesis to a bone. The method may include the steps of providing at least one of a model of the prosthesis 201, a model of the bone 202, and a model of a volume of bone to be removed 203 to accommodate the coupling of the prosthesis to the bone, and/or optionally receiving input based on user discretion 234 in generating the cut file.

Systems and Devices

FIG. 7 shows an exemplary embodiment of a computer system capable of performing functions for the methods described above. The computer system in this embodiment includes an input device 301, a display device 302 an output device 304, a user interface device 303, and a central processing unit. 300 In some embodiments, the input device 301 is capable of receiving data 305 from an image of a bone and/or a design of a prosthesis for a bone. In some embodiments, the display device 302 is capable of providing data for one or more of a model of a bone, a model of a prosthesis, a model of a volume of bone to be removed, a simulation of the model of the bone with the model of the volume of the bone to be removed, a simulation of the model of the volume of bone to be removed with the model of the prosthesis, and a simulation of the model of the bone with the model of the prosthesis. In some embodiments, the output device 304 is capable of providing a cut file with cut parameters specifying a cut path for a volume of bone to be removed intended to accommodate the coupling of the prosthesis to the bone. In some embodiments, the user interface device 303 capable of receiving input based on user discretion in generating the cut file. In some embodiments, the central processing unit (CPU) 300 is capable of providing one or more of a model of the prosthesis, a model of the bone, and a model of a volume of bone to be removed to accommodate the coupling of the prosthesis to the bone, of generating a cut file with cutting parameters to specify at least one cut path configured to create the volume of bone to be removed and of receiving optional input based on user discretion in generating the cut file.

The embodiment shown in FIG. 7 is an example of many possible embodiments, and other embodiments may be capable of performing the same functions in a different layout. For instance, a tablet computer may be used in which the user-interface 303 and the display 302 are combined in a single entity. Also, the various components of the computer system do not have to be co-localized. For instance, the data files 305 may be stored in a cloud-based service, and the display 302 and user interface 303 may be connected through a phone line or Internet service, allowing off-site participation of a user 100.

While the computer system may be capable of performing the functions necessary for the methods of the invention, it is not required that all functions are used in every procedure. For instance, a user 100 may decide that the input from data files 305 are sufficient to plan the procedure, and choose not to use the option to provide user-specified input.

In some embodiments, the CPU 300 may be of a dedicated design, exclusively configured to perform those functions. In other embodiments the CPU 300 may be capable of performing additional tasks in addition to being capable of the functions of the methods of the invention. Advantageously, such additional tasks may include Internet search capability, literature searching, communicating through e-mail and other Internet enabled communication means, calculations, and other tasks a user 100 may deem desirable. Alternatively, the CPU 300 may be of any other suitable design that is capable performing the functions necessary for the methods of the invention.

The invention is not limited to a specific number or type of CPU. The computer may contain a single CPU, or multiple CPUs or specialized CPU like a dual core CPU. The computer system is not limited to the use of a single computer. Under the scope of the invention, the computer system may employ multiple computers to perform the functions necessary for the methods of the invention.

In the exemplary embodiment of FIG. 7, the CPU 300 is capable of receiving input from external data files 305. The input can be provided in machine-readable code, and in any form that can be transformed into machine-readable code, for instance speech or text input. The invention does not put limits on the form in which the input can be provided.

Examples of input devices 301 include tangible media, like CD, DVD or flash drive, or direct input from other computer-driven systems like cloud-based services or other Internet enabled communication. Advantageously, the input may contain information about the one or more devices, such as prostheses, that are considered for the procedure, and information about the target body part, such as a bone, to receive the device. In specific inventive embodiments, external sources may be included in the data files 305 that contain additional information, such as relevant health records, literature data and the like.

The user interface device 303 can be based on any technology that generates machine-readable code. This can include the use of a mouse, a keyboard, tangible media, like CD, DVD or flash drive, direct input from other computer-driven systems like cloud-based services or other Internet enabled communication, as well as speech or text input.

The display devices 302 enable the CPU 300 to provide a user 100 with means to evaluate possible approaches to the surgical procedure. For instance, 3-D renditions of a bone model, a prosthesis model, a volume model may be provided, as well as, for instance, a 3-D simulation of various placements of a volume model in a bone model. Other display devices 302 may show results of dimensional calculations, safety limits, and the like. The display device 302 may advantageously be a computer screen, but other displays, like print-outs, are included in the scope of the invention.

Results of the functions of the CPU 300 may be exported through any number of output devices, like USB, CD, DVD and wireless outputs.

One output of the CPU 300 may be a cut file 206 with cutting specifications for a cut path generated based on the input from external data files 305 and on user-specified input received through the user-interface 303.

The information may be used for a variety of purposes, such as to perform, to assist in a procedure involving a computer-assisted surgical robot, or to help optimize a manually procedure.

In an embodiment where the CPU 300 is capable of performing the functions illustrated in FIG. 5, the CPU 300 may generate a bounding volume 209 (shown in FIG. 5) from the prosthesis model 201 and compare the bounding model 209 with the contents of the cut file 206 in checkbox 208. The result of the comparison may become part of the input to the CPU 300, and the CPU may be capable of including the results in the display function 302.

In an embodiment where the CPU is capable of performing the functions illustrated in FIG. 6, the CPU may receive information from the computer-assisted surgical robot 104 as part of the input.

The following example illustrates one of the preferred embodiments of the capabilities of the planning computer 102.

The planning computer 102 may be configured to be capable of performing the following exemplary workflow (FIGS. 5 and 7):

Receiving image information 222 of a bone to be cut
    Receiving design information 221 of a prosthesis to be incorporated in the bone
    Generating a virtual 3-D model 202 of the bone
    Generating a virtual 3-D model 201 of the prosthesis
    Generating a virtual 3-D model 203 of the volume of bone to be removed ("Volume model")
    Generating model-with-model simulations 205.
    Displaying the various models and simulations on a display 302 for examination by a user.

Allowing the user to manipulate the position of the models in the simulations.

Generating a cut file, specifying cutting parameters for a cut path to remove the volume of bone required to incorporate the prosthesis in the bone.

Allowing a user 100 to provide input in the generation or modification of the cut file 206 based on input 234 defined at the discretion of the user.

Generating a bounding volume 209 for the volume model 203, based on the prosthesis model 201.

Comparing the bounding volume 209 with the volume model 203, and providing feedback 207 to a user 100 in case safety limits are approached or exceeded.

Providing the cut file 206 to a computer-assisted surgical robot 104 to perform or assist in the performance of the surgical procedure.

As a person skilled in the art will recognize from the previous detailed description and from the figures and claims, modifications and changes can be made to the preferred embodiments of the invention without departing from the scope of this invention defined in the following claims.

What is claimed is:

1. A method for coupling of a prosthesis to a bone, the method comprising:
    providing one or more of a model of the prosthesis, a model of the bone, or a model of a volume of bone to be removed to accommodate the coupling of the prosthesis to the bone;
    providing a pre-existing cut file based on the model of the prosthesis, with cutting parameters to specify at least one cut path configured to create a volume of bone to be removed to receive the prosthesis;
    a user providing a user-specified input to modify the pre-existing cut file, the user-specified input including modifications of at least one of: precut, depth of cut, length of cut, diameter of cut path, regions to be cut, number of cut paths, shapes of cut paths, and types and sizes of cutters to be used so as to create a modified cut file;
    providing feedback, preoperatively, to the user if a volume of bone to be removed as specified by the modified cut file exceeds the volume of bone to be removed as specified by the pre-existing cut file;
    robotically cutting the bone according to the modified cut file;
    pausing the robotic cutting to further modify the user-specified input; and
    coupling the prosthesis to the bone.

2. The method of claim 1, wherein the model of the volume of bone to be removed is generated from the model of the bone.

3. The method of claim 1, further comprising generating a simulation of the model of the bone overlaid with the model of the volume of bone to be removed.

4. The method of claim 1, further comprising generating a simulation of the model of the volume of bone to be removed with the model of the prosthesis.

5. The method of claim 4, wherein the model of the prosthesis is positioned at least partially within the model of the volume of bone to be removed.

6. The method of claim 1, further comprising generating a simulation of the model of the bone with the model of the prosthesis.

7. The method of claim 6, wherein the model of the prosthesis is positioned at least partially within the model of bone.

* * * * *